United States Patent
Algeskog et al.

(10) Patent No.: US 10,668,054 B2
(45) Date of Patent: Jun. 2, 2020

(54) LIQUID COMPOSITION FOR WASH OF SCALP AND AND HAIR, OR FOR WASH OF SKIN

(71) Applicant: Daxxin AB, Västra Frölunda (SE)

(72) Inventors: Hans Algeskog, Västra Frölunda (SE); Henrik Lindau, Västra Frölunda (SE); Sten Ottander, Göteborg (SE)

(73) Assignee: DAXXIN AB, Västra Frölunda (SE)

( * ) Notice: Subject to any disclaimer, the term of this patent is extended or adjusted under 35 U.S.C. 154(b) by 0 days.

(21) Appl. No.: 16/017,782

(22) Filed: Jun. 25, 2018

(65) Prior Publication Data

US 2018/0369218 A1 Dec. 27, 2018
US 2019/0321347 A9 Oct. 24, 2019

(30) Foreign Application Priority Data

Jun. 27, 2017 (SE) ...................................... 1700132

(51) Int. Cl.

| | |
|---|---|
| A61K 31/4412 | (2006.01) |
| A61P 17/06 | (2006.01) |
| A61K 9/00 | (2006.01) |
| A61K 47/26 | (2006.01) |
| A61K 47/36 | (2006.01) |
| A61K 8/49 | (2006.01) |
| A61Q 5/00 | (2006.01) |
| A61Q 5/02 | (2006.01) |
| A61K 8/73 | (2006.01) |
| A61Q 19/00 | (2006.01) |
| A61Q 19/10 | (2006.01) |
| A61K 8/04 | (2006.01) |
| A61P 31/10 | (2006.01) |

(52) U.S. Cl.
CPC .......... *A61K 31/4412* (2013.01); *A61K 8/044* (2013.01); *A61K 8/4926* (2013.01); *A61K 8/737* (2013.01); *A61K 9/0014* (2013.01); *A61K 47/26* (2013.01); *A61K 47/36* (2013.01); *A61P 17/06* (2018.01); *A61P 31/10* (2018.01); *A61Q 5/006* (2013.01); *A61Q 5/02* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| | | |
|---|---|---|
| 7,262,158 B1 | 8/2007 | Lukenbach et al. |
| 8,431,601 B2 | 4/2013 | Mastrodonato |
| 9,943,468 B2 | 4/2018 | Stevenson |
| 2003/0133899 A1 | 7/2003 | Fan et al. |
| 2008/0206159 A1 | 8/2008 | Tamarkin et al. |

FOREIGN PATENT DOCUMENTS

| | | | |
|---|---|---|---|
| EP | 2 705 847 A1 | 3/2014 | |
| FR | 2694694 | 2/1994 | |
| WO | 98-52518 | 11/1998 | |
| WO | 2005037275 A1 | 4/2005 | |
| WO | WO 2009/074366 A1 * | 6/2009 | ............. A61K 8/362 |
| WO | 2014173659 A1 | 10/2014 | |

OTHER PUBLICATIONS

Google English machine translation of WO 2009/074366 A1 (Jun. 18, 2009) retrieved from the internet Feb. 17, 2019.*
Extended European Search Report for Application No. 18178512.2, dated Oct. 30, 2018.
Database GNPD [Online] MINTEL; May 17, 2017, anonymous: "Anti Dandruff Soothing Shampoo," XP055515245, retrieved from www.gnpd.com.
Databse WPI Week 201446, Nov. 1, 2014, Thomson Scientific, London, GB; AN 2014-J95640, XP002785720, "Composition useful as cosmetic e.g. for moisturizing skin, and treating e.g. inflammations, acne, atopic dermatitis and psoriasis, comprises piroctone olamine, allantonin, dipotassium glycytthizinate, alpha-bisabolol and tocopherol acetate,".
Database GNPD [Online] MINTEL; Sep. 18, 2005, Daxxin: "Triple Acting Shampoo," XP055515251, retrieved from www.gnpd.com.
Swedish first office action, dated Jan. 23, 2018, from corresponding Swedish patent application No. 1700132-2.
Swedish office action, dated Jun. 19, 2018, from corresponding Swedish patent application No. 1700132-2.
Daxxin Triple acting shampoo. Datasheet [online]. Daxxin, Sep. 2015 [retrieved on Jan. 10, 2018]. Record ID 3456165. Retrieved from <http://www.gnpd.com>.
Sephora hair detox shampoo. Datasheet [online]. Sephora, Nov. 2009 [retrieved on Jan. 10, 2018]. Record ID 1194660. Retrieved from <http://www.gnpd.com>.

(Continued)

*Primary Examiner* — Brian J Davis
(74) *Attorney, Agent, or Firm* — Young & Thompson

(57) ABSTRACT

A liquid composition for use in the treatment of psoriasis or ichtyosis in the scalp, or for treatment of psoriasis or ichtyosis on other skin than the one on the scalp. The composition is used for wash of scalp or skin, and including at least: 13.5-24.0% Mild wash tensides, 1.0-4.7% Guar HydroxrypropyltrimoniumCloride, and 0.3-1.0% Piroctone Olamine. The composition is preferably washed away with liquid after use, but is preferably left to work for 2-5 minutes before it is washed away.

8 Claims, No Drawings

(56) References Cited

OTHER PUBLICATIONS

Interior lifestyle by Sessan. Datasheet [online]. Blog post, Nov. 23, 2015 [retrieved on Jun. 5, 2018]. Retrieved from http://www.sessanochprinsessan.com/shopping-tips/har-du-ocksa-kli-i-harbotten/.

Ganemo A., Test mot psoriasis i harbotten. Datasheet [online]. Daxxin, Nov. 2014 [retrieved Jun. 5, 2018]. Retrieved from http://www.daxxin.se/en-GB/bevisat-effektiv/test-mot-psoriasis-i-h%C3%A5rbotten-33712270.

Allman hudinformation. Datasheet [online]. Daxxin, Apr. 21, 2017 [retrieved Jun. 5, 2018]. Retrieved from https://web.archive.org/web/20170421215814/https://www.pdf.nu/PartnerInfo_hudlakare.asp?id=64.

Daxxin antidandruff schampoo. Datasheet [online]. Daxxin, Mar. 7, 2017 [retrieved Jun. 5, 2018]. Retrieved from hittps://web.archive.org/web/20170307053422/http://www.daxxin.se/en/products/anti-dandruff-shampoo-25893050.

\* cited by examiner

LIQUID COMPOSITION FOR WASH OF SCALP AND AND HAIR, OR FOR WASH OF SKIN

TECHNICAL AREA

The present invention relates to a liquid composition for wash of scalp and hair or for wash of skin and aimed at alleviating dermatological disorder or disease, the composition comprising at least:
13.5-24.0% Mild wash tensides,
1.0-4.7% Guar HydroxrypropyltrimoniumCloride,
0.3-1.0% Piroctone Olamine
The composition is aimed at use to alleviate psoriasis in the scalp or on other skin, to alleviate eczema or to alleviate ichtyosis.

BACKGROUND

There are a number of dermatological diseases, that are difficult or impossible to remedy. The treatment therefore aims at alleviating the symptoms or the troubles for a very long time, possibly for an entire life. Of course it is important that the symptoms are indeed alleviated and that the treatment itself is not trying. If so the life quality of the affected is raised.
Psoriasis is such a skin disease. It gives red spots, that scales off and sometimes itches. The outermost layer of the skin is called the epidermis. Outermost in it the horn layer is situated, that is made up of dead skin cells. From beneath new skin cells in a steady pace replaces old dead skin cells that falls off. In a psoriasis condition the cells in the epidermis are formed more quickly than usual, and the cells do not fall off one by one but flakes off in big flakes. Furthermore there is an inflammation in the skin that increases the blood circulation to redden the skin and warm it. Psoriasis often comes in so called relaps. It implies periods with small or no problems and periods when the disease flushes up and the rashes becomes bigger.
The most common form of psoriasis shows round, a couple of centimeter big flaking rashes, so called plaques. It is therefore called plaque-psoriasis. The skin disorders can be located anywhere on the whole body, but most often on the elbows, the knees, the lower part of the back and the scalp. The coverage of the body can vary from only less than a percent up to the whole or almost the whole body surface. In a mild form of psoriasis, that can be seen as a skin disorder, it can be sufficient to take a bath and to apply a thick layer of softening lotion or ointment several times a week.
In a more severe form of psoriasis, that should be regarded as a skin disease, a more effective treatment is often wanted using prescribed lotions and ointments. These products can comprise D-vitamin like substances, that have few side effects. But most times these products comprise a strong cortisone, that works fast but has side effects. To reduce the troubles regular treatment is needed for several weeks. After the treatment the rashes will often come back after only a couple of weeks. The side effects make these substances not suitable to use for pregnant and nursing women. There are also compositions that comprise a number of other ingredients to try to decrease the side effects of the strong cortisone. and dampen its negative influence on the skin. EP 2 705 847 gives an example of a night cream that in addition to a strong cortisone also comprises a tar extract, an antibiotic component and lanolin, och preferably also almond oil. Furthermore it is preferable to use a day cream that comprises skin caring and skin calming vegetabilic oils. Combined with washing of the skin this makes three different treatment steps. After 3 months of treatment each one of 3 subjects were three from psoriasis symptoms for almost 1 year before the symptoms started again.
To treat psoriasis in the scalp a de-scaling anti-dandruff shampoo or a solvent that comprises cortisone is used. The treatment takes away all dead skin or scales. These compositions are fairly aggressive to the skin and are therefore often combined with a sothening and skin calming lotion. But in spite of complicated multi-stage treatments the problems as a rule come back after only a few weeks. This also applies for other skin disorders or skin diseases as eczema on the skin or ichtyosis. There is a need for compositions and treatments that can provide good results at the same time as they are less aggresive to the skin and give less side effects than the current compositions At the same time the treatments should preferably be easy to perform for the sick person.

SUMMARY

The present invention intends to decrease one or more of the above stated weaknesses by providing a liquid composition for washing of the scalp and hair or for washing of skin and aimed at alleviating dermatological disorder or disease, the composition comprising at least:
13.5-24.0% Mild wash tensides,
1.0-4.7% Guar HydroxrypropyltrimoniumCloride,
0.3-1.0% Piroctone Olamine
Further the liquid composition can preferably be washed away with liquid, and preferably after it has been applied for 2-5 minutes before it is washed away with liquid. The use of the composition is preferably made where the dermatological disorder or disease is psoriasis on the scalp or on other skin. The use of the composition is preferably made where the dermatological disorder or disease is eczema on the skin or ichtyosis.

DESCRIPTION OF PREFERRED EMBODIMENTS

The liquid composition according to the current invention comprises at least:
13.5-24.0% Mild wash tensides,
1.0-4.7% Guar HydroxrypropyltrimoniumCloride, Below called Guar
0.3-1.0% Piroctone Olamine
The use of mild wash tensides, results in less dry out of the skin, compared to a use of sulfates, which is the most usual. The wash results in that only a part of the dead skin cells or dead skin flakes is washed away, and definitely not all of them as a de-flaking shampoo does. This provides a wash more gentle for the skin. Furthermore Guar comprises substances that are conditioning by being softening and remoisturising
Furthermore Piroctone Olamine is an active ingredients that slows down the growth of the fungus *Malassezia furfur*. To much of this fungus creates or contributes to scalp problems The liquid composition washes gently to not dry out the skin, and it is softening and remoisturing and it slows the growth of fungus. All this makes the present composition much more gentle than earlier compositions that did take away all dead skin cells and all fungus. After use of such an earlier composition a complementary cream treatment was required to remoisturize and soften. But still the treatment with an earlier composition and lotion is fairly aggresive.

The new liquid composition enables a treatment that is much milder to the skin, so the skin is not irritated. Also it enables a treatment in a single stage in stead of normally in 2 or 3 stages. You can see it as a change of paradigm into a more gentle and simple treatment. Tests made show that this especially is the case if the amount of Guar is increased to 1.5%-3.5%, or preferably 1.5%-3.0%. At the same time the amount of Piroctone Oleamine should be increased to 0.5%-0.97%, or preferably 0.7%-0.97%. In the tests made no known side effects were noted.

The mild wash tensides are one or more of the following wash tensides:

Disodium Laureth Sulfosuccinate
Lauryl Gluciside
Disodium Undecylenamido Mea Sulfosuccinate
Cocamidpropyl Betain They have been chosen as they are kind to the skin and do not dry the skin out.

Use of a liquid composition according to the present invention, where the dermatological disorder or disease is psoriasis in the scalp and the composition is a shampoo or similar. Psoriasis in the scalp is very irritating for the affected person. The affected person has a need to keep his hair and scalp clean. Of course it is an advantage if the wash can be made with a mild shampoo, that does not irritate the scalp, and leads to itch and pruritus. The composition according to the invention can in more severe cases be combined with aq cortisone drug, but in many cases the composition can give a good result when used alone, see studies below. The treatment of the affected person is particularly simple in this case. He only changes his earlier shampoo to a shampoo according to the invention Use of a composition according to the present invention, where the dermatological disorder or disease is psoriasis on other skin than the skin of the scalp and the composition is a shower gel, shower cream or similar. As the composition is mild to the skin and without known side effects it can be used over the whole body and replace a usual shower cream. Limited tests with the composition used at psoriasis on other skin than in the scalp have showed good results. Test persons for Psoriasis in the scalp that also have psoriasis on other skin have simply noticed that the composition works well for both types of psoriasis, which is perhaps not so strange.

Use of a composition according to the present invention where the dermatological disorder or disease is eczema in the scalp or on other skin and the composition is a shampoo, shower cream or similar. As the composition is mild to the skin and without known side effects it can be used over the whole body and replace a usual shower cream. Limited tests have shown good results for the type of eczema Seborroic eczema, i.e. Eczema in the scalp.

Use of a composition according to the present invention, where the dermatological disorder or disease is ichtyosis on the scalp or on other skin and the composition is a shampoo, a shower cream or similar. Limited test with the composition for this aim have given good results for more than 10 persons having the diagnosis ichtyosis on the scalp. Use of a composition according to the present invention, where the composition is washed away with liquid after use. Normally the liquid is water, but of course additives can be used, e.g. Almond oil. Please observe that made studies have used water for wash away. Use of a composition as above for wash of scalp or skin, whereby the composition is left to work for 2-5 minutes before it is washed away with liquid. This last use has been considered the best and has also been recommended to the subjects in the made studies.

Studies

A study has been made for persons with the diagnosis psoriasis in the scalp. More than 50 persons have been using a shampoo according to the invention for 3 months. They have filled in a test protocol before and after the 3 months treatment. In short the result show that approximately 60% of the subjects experienced an improvement through a decrease of their symptoms noted as better or much better. This concerned symptoms of the four types itching, reddening, scaling and scratch marks/wounds.

A limited study of more than 10 persons having ichtyosis on the scalp shows that a clear majority experienced a distinct reduction of their symptoms after a 7 week treatment with the shampoo according to the invention. Everybody would also continue using the shampoo.

The invention claimed is:

1. A method of treating psoriasis, comprising applying one of i) a shampoo for wash of scalp and hair in the treatment of psoriasis in the scalp, and ii) a shower gel or shower soap for wash of skin in the treatment of psoriasis on skin other than the scalp, wherein the shampoo, the shower gel, and the shower soap are comprised of a liquid composition, comprising:
   3.5-24.0% by weight non-sulfate wash tensides,
   1.0-4.7% by weight Guar Hydroxypropyltrimonium Chloride, and
   0.3-1.0% by weight Piroctone Olamine.

2. The method of claim 1, wherein the composition is washed away with liquid after use.

3. The method of claim 1, wherein the composition is left to work for 2-5 minutes before being washed away with liquid.

4. The method of claim 1, wherein the composition is used as the only treatment stage.

5. A method of treating ichtyosis, comprising applying one of i) a shampoo for wash of scalp and hair in the treatment of ichtyosis in the scalp, and ii) a shower gel or shower soap for wash of skin in the treatment of ichtyosis on skin other than the scalp, wherein the shampoo, the shower gel, and the shower soap are comprised of a liquid composition, comprising:
   3.5-24.0% by weight non-sulfate wash tensides,
   1.0-4.7% by weight Guar Hydroxypropyltrimonium Chloride, and
   0.3-1.0% by weight Piroctone Olamine.

6. The method of claim 5, wherein the composition is washed away with liquid after use.

7. The method of claim 5, wherein the composition is left to work for 2-5 minutes before being washed away with liquid.

8. The method of claim 5, wherein the composition is used as the only treatment stage.

* * * * *